United States Patent [19]
Jaen et al.

[11] Patent Number: 4,739,067
[45] Date of Patent: Apr. 19, 1988

[54] 4-(1,2,5,6-TETRAHYDRO-1-ALKYL-3-PYRIDINYL)-2-THIAZOLAMINES AND 4-(HEXAHYDRO-1-ALKYL-3-PYRIDINYL)-2-THIAZOLAMINES

[75] Inventors: Juan C. Jaen, Plymouth; Lawrence D. Wise, Ann Arbor; Haile Tecle, Ann Arbor; Stephen C. Bergmeier, Ann Arbor, all of Mich.

[73] Assignee: Warner-Lambert Company, Morris Plains, N.J.

[21] Appl. No.: 925,760

[22] Filed: Oct. 31, 1986

Related U.S. Application Data

[62] Division of Ser. No. 803,697, Dec. 2, 1985, Pat. No. 4,650,805.

[51] Int. Cl.$^4$ ................ C07D 417/04; A61K 31/425
[52] U.S. Cl. .................................... 546/280; 514/321; 514/342
[58] Field of Search ................................ 546/209, 280

[56] References Cited

U.S. PATENT DOCUMENTS 4,650,805  3/1987  Jaen et al. ............................ 514/326

FOREIGN PATENT DOCUMENTS 117082A   8/1984  European Pat. Off. ............ 546/280
3247118   6/1984  Fed. Rep. of Germany ...... 546/277
58-035186 3/1983  Japan ................................. 546/280

Primary Examiner—Robert T. Bond
Attorney, Agent, or Firm—Elizabeth M. Anderson

[57] ABSTRACT

A unique series of 4-(1,2,5,6-tetrahydro-1-alkyl-3-pyridinyl)-2-thiazolamines and 4-(hexahydro-1-alkyl-pyridinyl)-2-thiazolamines are disclosed. These compounds are useful as dopaminergic agents. Intermediates for preparing the compounds, pharmaceutical compositions containing them, and methods for using the pharmaceutical compositions for treating human psychosis, elevated blood pressure, Parkinson's disease, hyperprolactinaemia, sexual disorders, and acromegaly are described.

4 Claims, No Drawings

4-(1,2,5,6-TETRAHYDRO-1-ALKYL-3-PYRIDINYL)-2-THIAZOLAMINES AND 4-(HEXAHYDRO-1-ALKYL-3-PYRIDINYL)-2-THIAZOLAMINES

This is a divisional application of U.S. Ser. No. 803,697, filed Dec. 2, 1985, now U.S. Pat. No. 4,650,805 issued Mar. 12, 1987.

BACKGROUND OF THE INVENTION

The compounds of the instant invention are a unique series of 4-(1,2,5,6-tetrahydro-1-alkyl-3-pyridinyl)-2-thiazolamines and 4-(hexahydro-1-alkyl-3-pyridinyl)-2-thiazolamines which are useful as dopaminergic agents, antipsychotics, and antihypertensives.

European patent application No. 117,082 discloses 4,5-disubstituted thiazole derivatives having cardiotonic and antiulcer activity.

Japanese Kakai No. 58/035186 discloses certain dicarboxyaminothiazole derivatives having certain immunocontrolling power.

West German application No. 3247118A discloses substituted 1,4-dihydropyridine derivatives with cardiovascular and antagonistic properties.

SUMMARY OF THE INVENTION

One aspect of the present invention is a compound of the formula

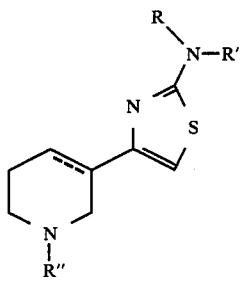

wherein === signifies the presence of a single or double bond between two carbon atoms; R is H or a straight or branched alkyl of from one to four carbon atoms; R' is H, a straight or branched alkyl of from one to four carbon atoms, or CO—R''' where R''' is a straight or branched alkyl of from one to four carbon atoms; R'' is a straight or branched alkyl group of from one to eight carbon atoms, a straight or branched alkenyl group of from two to eight carbon atoms, an aralkyl group wherein the alkyl is straight or branched of from one to four carbon atoms, or a group of the formula —(CH$_2$)$_n$—O—(CH$_2$)$_m$—CH$_3$ wherein n and m are each independently zero to four, or a pharmaceutically acceptable acid addition salt thereof, or the stereoisomers thereof when === is a single bond.

Another aspect of the present invention is a method of preparing a compound of Formula III which comprises:

(a) treating a pyridinyl-thiazolamine with an organic halide to product the corresponding 1-substituted pyridinium salt;

(b) reducing selectively the salt to form the corresponding 1,2,5,6-tetrahydropyridinylthiazolamine, and if desired;

(c) treating this thiazolamine with an acid anhydride to form an N-substituted acid amide; and (d) converting the product of step b or c, if desired, to a pharmaceutically acceptable acid addition salt.

A third aspect of the present invention is another method of preparing a compound of Formula III which comprises:

(a) treating an N-alkyl piperidine 3-carboxylic acid ester with lithium hydroxide to form the corresponding salt;

(b) reacting the salt with methyllithium to produce the corresponding 3-acetyl-N-alkyl-piperidine;

(c) mixing the piperidine with thiourea and halogen to form the corresponding thiazolamine;

(d) treating the thiazolamine with an acid anhydride to form the N-substituted acid amide; and (e) converting the product of step c or d, if desired, to a pharmaceutically acceptable acid addition salt.

A fourth aspect of the present invention is a pharmaceutical composition which comprises an effective amount of a compound of structural Formula III above in combination with a pharmaceutically acceptable carrier.

A fifth aspect of the present invention is a method of inhibiting prolactin secretion in mammals, i.e., being useful in the treatment of hyperprolactinaemia, galactorrhoea, amenorrhoea, menstrual disorders and impotence, comprising administering to the mammal the above identified pharmaceutical composition in unit dosage form.

A sixth aspect of the present invention is a method of treating hypertension in a mammal comprising administering to the mammal the above identified pharmaceutical composition in unit dosage form.

A seventh aspect of the present invention is a method of treating psychosis, i.e., schizophrenia or drug-induced, in a mammal comprising administering the above identified pharmaceutical composition in unit dosage form.

A eighth aspect of the present invention is a method of treating disorders of the central nervous system, i.e., Parkinson's disease and depression, in mammals comprising administering the above identified pharmaceutical composition in unit dosage form.

DETAILED DESCRIPTION OF THE INVENTION

Compounds of the formula

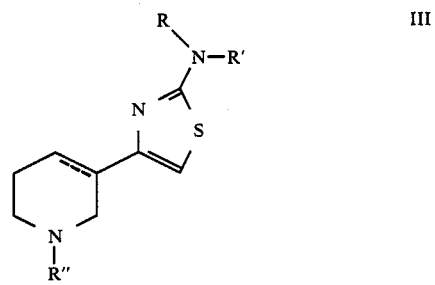

described above, comprise the present invention.

The compounds include solvates and hydrates and pharmaceutically acceptable salts of the compounds of the above formula.

The term pharmaceutically acceptable acid addition salt is intended to mean a relatively non-toxic acid addition salt, either from inorganic or organic acids such as, for example, hydrochloric, sulfuric, phosphoric, acetic, citric, oxalic, malonic, salicylic, malic, gluconic, fumaric, succinic, ascorbic, maleic, methanesulfonic, and the like. The salts are prepared by contacting the free base form with a sufficient amount of the desired acid to product a salt in the conventional manner.

The free base forms, may be regenerated by treating the salt form with a base.

The alkyl and alkenyl groups of the present invention comprise both straight and branched carbon chains of from one to eight carbon atoms. Representatives of such groups are methyl, ethyl, propyl, isopropyl, butyl, 3-methylbutyl, pentyl, and the like.

The aralkyl groups of the present invention comprise alkyl groups which are both straight and branched carbon chains of from one to four carbon atoms and aryls such as phenyl or phenyl substituted by lower alkyl, lower alkoxy, lower thioalkoxy, halogen, or trifluoromethyl; aryl can also be a heterocycle such as 2-, 3-, or 4-pyridinyl; 2-, 4-, or 5-pyrimidinyl, or 2-pyrazinyl.

The present invention also includes each individual stereoisomer of the compounds depicted by Formula III, when === represents a single bond.

The preferred compounds are those of Formula III where R is hydrogen or an alkyl of from one to four carbon atoms, where R' is hydrogen or CO—R,''' where R'' is an alkyl of from one to eight carbon atoms, an alkenyl group of from two to eight carbon atoms, an aralkyl group or a group of the formula —(CH$_2$)$_n$—O—(CH$_2$)$_m$—CH$_3$ wherein n and m are each independently zero to four and where R''' is an alkyl of from one to four carbon atoms.

The more preferred compounds for the treatment of hypertension, inhibition of prolactin secretion, Parkinson's disease and depression are those of Formula III where R is hydrogen, R' is hydrogen or CO—R,''' R'' is an alkyl group from one to three carbon atoms or an alkenyl group from two to three carbon atoms and R''' is an alkyl group from one to three carbon atoms. The more preferred compounds for the treatment of psychosis, i.e., schizophrenia, are those of Formula III where R is hydrogen, R' is hydrogen or CO—R,''' R'' is an alkyl or alkenyl group from four to six carbon atoms and R''' is an alkyl group from one to three carbon atoms.

Particularly valuable compounds falling within the scope of the present invention include the following compounds:

4-(1,2,5,6-tetrahydro-1-propyl-3-pyridinyl)-2-thiazolamine;
4-(1,2,5,6-tetrahydro-1-methyl-3-pyridinyl)-2-thiazolamine;
4-(1,2,5,6-tetrahydro-1-ethyl-3-pyridinyl)-2-thiazolamine;
4-(1,2,5,6-tetrahydro-1-allyl-3-pyridinyl)-2-thiazolamine;
4-(1,2,5,6-tetrahydro-1-butyl-3-pyridinyl-2-thiazolamine;
4-(1,2,5,6-tetrahydro-1-pentyl-3-pyridinyl)-2-thiazolamine;
4-(1,2,5,6-tetrahydro-1-hexyl-3-pyridinyl)-2-thiazolamine;
4-(1,2,5,6-tetrahydro-1-heptyl-3-pyridinyl)-2-thiazolamine;
4-[1,2,5,6-tetrahydro-1-(3-methylbutyl)-3-pyridinyl]-2-thiazolamine;
4-[1,2,5,6-tetrahydro-1-(2-phenylethyl)-3-pyridinyl]-2-thiazolamine;
4-[1-(2-ethoxyethyl)-1,2,5,6-tetrahydro-3-pyridinyl]-2-thiazolamine;
N-[4-(1,2,5,6-tetrahydro-1-pentyl-3-pyridinyl)-2-thiazolyl]-acetamide;
N-[4-(1,2,5,6-tetrahydro-1-propyl-3-pyridinyl)-2-thiazolyl]-acetamide;
N-methyl-4-(1,2,5,6-tetrahydro-1-propyl-3-pyridinyl)-2-thiazolamine;
N-methyl-4-(1,2,5,6-tetrahydro-1-butyl-3-pyridinyl)-2-thiazolamine;
N-methyl-4-(1,2,5,6-tetrahydro-1-pentyl-3-pyridinyl)-2-thiazolamine;
N-methyl-N-[4-(1,2,5,6-tetrahydro-1-propyl-3-pyridinyl)-2-thiazolyl]-acetamide;
N-methyl-N-[4-(1,2,5,6-tetrahydro-1-pentyl-3-pyridinyl)-2-thiazolyl]-acetamide;
4-(1-propyl-3-piperidyl)-2-thiazolamine;
N-[4-(1-propyl-3-piperidyl)-2-thiazolyl]-acetamide;
4-(1-propyl-3R-piperidyl)-2-thiazolamine; and
4-(1-propyl-3S-piperidyl)-2-thiazolamine.

The above compounds may be prepared by treating a pyridinyl-thiazolamine with an organic halide to form the corresponding 1-substituted pyridinium salt; the reaction is carried out in ethyl alcohol or acetonitrile and is heated at reflux for 18 to 30 hours. Then the pyridinium salt is selectively reduced to form the corresponding tetrahydropyridinylthiazolamine. This step takes place in an alcohol-water mixture at −10° to +10° C. with a reducing agent. If desired, one can treat this thiazolamine with an acid anhydride to form an N-substituted acid amide and then convert the product, if desired, to a pharmaceutically acceptable acid addition salt.

In the preferred reaction conditions, the thiazolamine and the organic halide are refluxed in absolute ethanol or acetonitrile for 24 hours. The preferred halides are 1-bromopropane, ethyl iodide, allyl bromide, 1-bromobutane, 1-bromopentane, 1-bromohexane 1-bromoheptane, 1-bromo-3-methylbutane, (2-bromoethyl)benzene, or 2-bromoethyl ethyl ether. One may also use an organic p-toluenesulfonate in place of the organic halide to form the intermediate pyridinium salt.

The resulting 1-substituted pyridinium salt may be selectively reduced in a 1:1 water:methanol solution by a slow addition of excess sodium borohydride over a period of thirty minutes. The preferred method of preparing the amide is by dissolving the substituted thiazolamine in an acid anhydride containing anhydrous sodium acetate. Heat this under reflux in nitrogen for three hours.

The following is the schematic procedure illustrating the process.

SCHEME I

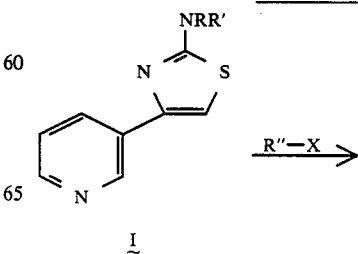

-continued
SCHEME I

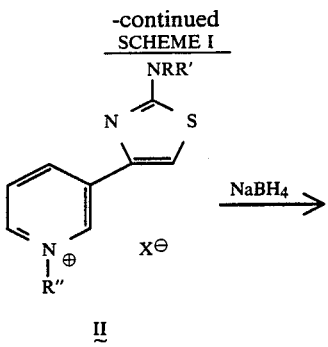

II

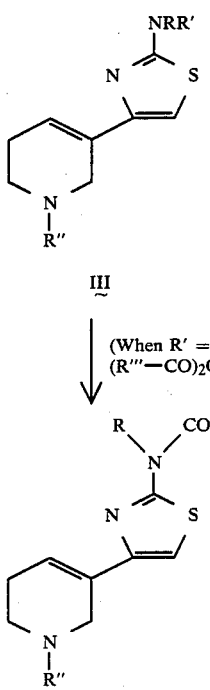

III

III (R' = R'''—CO)

The hexahydro-compounds of the instant invention may be prepared by treating 3-acetyl-N-alkylpyridines with a thiourea, in the presence of a halogenating agent such as bromine or iodine, to form the corresponding thiazolamines.

The reaction is carried out at 90°–110° C. for 18–30 hours. Preferably, the reactions at 100° C. for 24 hours.

The substituted thiazolamine may be converted, if desired, to an N-substituted acide amide by reaction of the thiazolamine with an acid anhydride. Preferably one uses refluxing acetic anhydride for two hours to produce the acetamide. The following schematic procedure describes these reactions.

SCHEME II

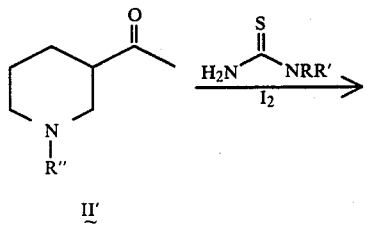

II'

-continued
SCHEME II

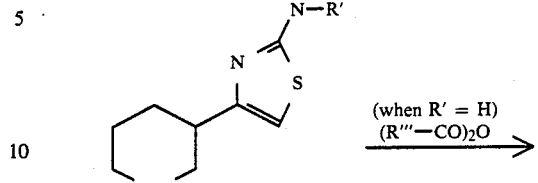

III

III (R' = R'''—CO)

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders or tablet disintegrating agents; it can also be encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 to 10 to about 70 percent of the active ingredient. Suitable solid carriers are magnesium carbonate, magnesium stearate, talc, sugar, lactose, pectin, dextrin, starch, gelatin, tragacanth, methylcellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

For preparing suppositories, a low melting wax such as a mixture of fatty acid glycerides or cocoa butter is first melted, and the active ingredient is dispersed homogenously therein by stirring. The molten homogeneous mixture is then poured into convenient sized molds, allowed to cool, and thereby solidify.

Liquid form preparations include solutions, suspensions, and emulsions. As an example may be mentioned water or water propylene glycol solutions for parenteral injection. Liquid preparations can also be formulated in solution in aqueous polyethyleneglycol solution. Aqueous solutions suitable for oral use can be prepared by dissolving the active component in water and adding suitable colorants, flavors, stabilizing, and thickening agents as desired. Aqueous suspensions suitable for oral use can be made by dispersing the finely divided active component in water with viscous material, i.e., natural or synthetic gums, resins, methylcellulose, sodium carboxymethylcellulose, and other well-known suspending agents.

Also included are solid form preparations which are intended to be converted, shortly before use, to liquid form preparations for either oral or parenteral administration. Such liquid forms include solutions, suspensions, and emulsions. These particular solid form preparations are most conveniently provided in unit dose form and as such as used to provide a single liquid dosage unit. Alternatively, sufficient solid may be provided so that after conversion to liquid form, multiple individual liquid doses may be obtained by measuring predetermined volumes of the liquid form preparation as with a syringe, teaspoon, or other volumetric container. When multiple liquid doses are so prepared, it is preferred to maintain the unused portion of said liquid doses at low temperature (i.e. under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents, and the like. The liquid utilized for preparing the liquid form preparation may be water, isotonic water, ethanol, glycerine, propylene glycol, and the like, as well as mixtures thereof. Naturally, the liquid utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets capsules, and powders in vials or ampoules. The unit dosage form can also be a capsule, cachet, or tablet itself, or it can be the appropriate number of any of these in packaged form.

The quantity of active compound in a unit dose of preparation may be varied or adjusted from 1 mg to 500 mg, preferably 5 to 100 mg according to the particular application and the potency of the active ingredient. The compositions can, if desired, also contain other compatible therapeutic agents.

In therapeutic use, the mammalian dosage range for a subject of 70 kg body weight is from 1 to 1500 mg per day or preferably 25 to 750 mg per day optionally in divided portions. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter the dosage is increased by small increments until the optimum effect under the circumstances is reached. For convenience, the total daily dosage may be divided and administered in portions during the day if desired.

The compounds of the present invention act on the dopamine systems of the mammalian body. Some are dopamine agonists, effective against, for example, hyperprolactinoemia, Parkinson's disease, hypertension, sexual disorders, and acromegaly. Others are dopamine antagonists, effective as antipsychotic agents.

The method for determining the effectiveness of the compounds of the instant invention as dopaminergic agents is explained in *Mol. Pharmacol.*, 1976 (12) 800 herein incorporated by reference. Table 1 below sets forth the results.

TABLE 1

| Haloperidol Receptor Binding (% inhibition at $10^{-6}$ M) | |
|---|---|
| Compound | % Inhibition |
| III (where -- is double bond) | |
| $R=R'=H; R''=CH_3$ | 50 |
| $R=R'=H; R''=CH_2CH_3$ | 49 |
| $R=R'=H; R''=(CH_2)_2CH_3$ | 66 |
| $R=R'=H; R''=(CH_2)_3CH_3$ | 57 |
| $R=R'=H; R''=(CH_2)_4CH_3$ | 26 |
| $R=R'=H; R''=(CH_2)_5CH_3$ | 88 |
| $R=R'=H; R''=(CH_2)_6CH_3$ | |
| $R=R'=H; R''=CH_2CH=CH_2$ | 40 |
| $R=R'=H; R''=(CH_2)_2OCH_2CH_3$ | 35 |
| $R=R'=H; R''=(CH_2)_2Ph$ | 16 |
| $R=R'=H; R''=(CH_2)_2CH(CH_3)_2$ | 65 |
| $R=Me; R'=H; R''=(CH_2)_2CH_3$ | Not available |
| $R=Me; R'=H; R''=(CH_2)_3CH_3$ | Not available |
| $R=Me; R'=H; R''=(CH_2)_4CH_3$ | Not available |
| $R=H; R'=COCH_3; R''=(CH_2)_2CH_3$ | 0 |
| $R=H; R'=COCH_3; R''=(CH_2)_4CH_3$ | 0 |
| $R=Me; R'=COCH_3; R''=(CH_2)_2CH_3$ | Not available |
| $R=Me; R'=COCH_3; R''=(CH_2)_4CH_3$ | Not available |
| III (where -- is single bond) | |
| $R=R'=H; R''=(CH_2)_2CH_3$ | 15 |
| $R=H; R'=COCH_3; R''=(CH_2)_2CH_3$ | 9 |

The effects of representative compounds of the present invention as antipsychotic agents was established by the Mouse Activity and Screen Test Procedure described in *Pharmacol. Biochem. Behav.* 1978 (8) 97, herein incorporated by reference. The results are shown in Table 2.

TABLE 2

| Inhibition of Locomotor Activity in Mouse ($ED_{50}$, mg/kg) | |
|---|---|
| Compound | $ED_{50}$ |
| III (where -- is double bond) | |
| $R=R'=H; R''=CH_3$ | 30 |
| $R=R'=H; R''=CH_2CH_3$ | >30 |
| $R=R'=H; R''=(CH_2)_2CH_3$ | 2.9 |
| $R=R'=H; R''=(CH_2)_3CH_3$ | 7.3 |
| $R=R'=H; R''=(CH_2)_4CH_3$ | <10 |
| $R=R'=H; R''=(CH_2)_5CH_3$ | >30 |
| $R=R'=H; R''=(CH_2)_6CH_3$ | 10.4 |
| $R=R'=H; R''=CH_2CH=CH_2$ | 3 |
| $R=R'=H; R''=(CH_2)_2OCH_2CH_3$ | 30 |
| $R=R'=H; R''=(CH_2)_2Ph$ | 18.1 |
| $R=R'=H; R''=(CH_2)_2CH(CH_3)_2$ | 8.7 |
| $R=Me; R'=H; R''=(CH_2)_2CH_3$ | 10 |
| $R=Me; R'=H; R''=(CH_2)_3CH_3$ | Not available |
| $R=Me; R'=H; R''=(CH_2)_4CH_3$ | <10 |
| $R=H; R'=COCH_3; R''=(CH_2)_2CH_3$ | 30 |
| $R=H; R'=COCH_3; R''=(CH_2)_4CH_3$ | 10 |
| $R=Me; R'=COCH_3; R''=(CH_2)_2CH_3$ | 39 |
| $R=Me; R'=COCH_3; R''=(CH_2)_4CH_3$ | 6.4 |
| III (where -- is single bond) | |
| $R=R'=H; R''=(CH_2)_2CH_3$ | 10 |
| $R=H; R'=COCH_3; R''=(CH_2)_2CH_3$ | 30 |

The methodology for testing the antihypertensive action of the compounds of the invention is described in *Am. J. Med. Sci.*, 1970 (259)257, herein incorporated by reference. These experiments are considered standard tests in mammals and are indicative of utility for treatment of similar diseases in humans.

TABLE 3

| Spontaneous Hypertensive Rat (30 mg/kg, PO) | | |
| --- | --- | --- |
| Compound | Decrease in Blood Pressure | Duration |
| 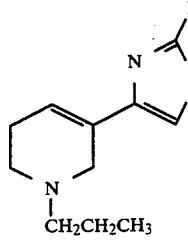 | 20% 10-15% | 1 hour up to 6 hours |
| 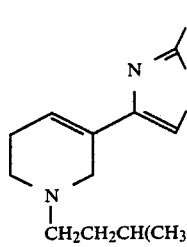 | 12-20% | up to 10 hours |

The following examples are provided to enable one skilled in the art to practice the present invention. These examples are not intended in any way to limit the scope of the invention, but are illustrative thereof.

EXAMPLE 1

4-(1,2,5,6-Tetrahydro-1-propyl-3-pyridinyl)-2-thiazolamine

A solution of 14.16 g of 4-(3-pyridinyl)-2-thiazolamine (A. Taurins and A. Blaga, J. Heterocyclic Chemistry, 1970 (7) 1137) and 50 g of 1-bromopropane in 500 ml absolute ethanol was heated at reflux for 24 hours. By this time, small amounts of a salt had begun to crystallize on the walls of the flask. The solution was concentrated to dryness on a rotary evaporator, leaving 30 g of a yellow solid, mp 259°–261° C., identified as 3-(2-amino-4-thiazolyl)-1-propylpyridinium bromide, hydrobromide.

A solution of 26 g of this salt in 300 ml water:methanol (1:1) was cooled in an ice bath and treated with 25 g of sodium borohydride, in small portions, over a period of 30 minutes. The cold bath was then removed and the mixture was stirred at room temperature overnight. The mixture was concentrated to about one half of the original volume and carefully acidified by dropwise addition of concentrated HCl. The resulting solution was made basic with concentrated ammonium hydroxide and extracted with ethyl acetate (3×75 ml). The organic layer was dried and concentrated, leaving a yellow oil which was chromatographed on Silica gel (2% NH4OH in ethyl acetate) to produce 4.4 g of the title compound, mp 121°–123° C. (dec).

EXAMPLE 2

4-(1,2,5,6-Tetrahydro-1-methyl-3-pyridinyl)-2-thiazolamine

By using the method of Example 1, but replacing the 1-bromopropane with methyl p-toluenesulfonate, the title compound was obtained as an oil which was dissolved in ether and treated with the appropriate amount of a saturated solution of hydrogen chloride in isopropanol to produce an overall 50% yield of its dihydrochloride, mp 272° C.

EXAMPLE 3

4-(1,2,5,6-Tetrahydro-1-ethyl-3-pyridinyl)-2-thiazolamine

By following the method of Example 1, using ethyl iodide as the alkylating agent, the title compound was produced, in 50% yield, as a tan solid, mp 116°–120° C.

EXAMPLE 4

4-(1,2,5,6-Tetrahydro-1-allyl-3-pyridinyl)-2-thiazolamine

When allyl bromide is used instead of the 1-bromopropane of Example 1, the title compound can be prepared. Following flash chromatography of the crude reaction mixture, one recrystallization from ethyl acetate was necessary to obtain a 30% overall yield of the compound as a light tan solid, mp 129°–132° C.

EXAMPLE 5

4-(1,2,5,6-Tetrahydro-1-butyl-3-pyridinyl)-2-thiazolamine

By replacing the 1-bromopropane of Example 1 with 1-bromobutane, the title compound was prepared as a tan solid (mp 220°–2° C.) which was converted to its dihydrochloride (mp 239°–240° C.) by the method described in Example 2.

EXAMPLE 6

4-(1,2,5,6-Tetrahydro-1-pentyl-3-pyridinyl)-2-thiazolamine

The title compound was obtained in 56% overall yield by using 1-bromopentane in the method described in Example 1. The free base was a reddish oil which crystallized when triturated with a small amount of isopropanol (mp 85°–87° C.). The dihydrobromide (mp 246°–247° C.) was prepared by a method similar to the one described in Example 2, using a saturated solution of hydrogen bromide in isopropanol.

EXAMPLE 7

4-(1,2,5,6-Tetrahydro-1-hexyl-3-pyridinyl)-2-thiazolamine

When using 1-bromohexane in the procedure of Example 1, instead of 1-bromopropane, the title compound is obtained as a red oil after chromatography. The method of Example 2 allows the formation of the dihydrochloride monohydrate, mp 200°–202° C.

EXAMPLE 8

4-(1,2,5,6-Tetrahydro-1-heptyl-3-pyridinyl)-2-thiazolamine

Repeating the method of Example 1 with 1-bromoheptane as the alkylating agent, followed by salt formation as described in Example 2, the dihydrochloride monohydrate of the title compound was obtained, mp 191°–193° C.

EXAMPLE 9

4-[1,2,5,6-Tetrahydro-1-(3-methylbutyl)-3-pyridinyl]-2-thiazolamine

The method of Examples 1 and 2 was repeated, using 1-bromo-3-methylbutane as the alkylating agent to produce the dihydrochloride monohydrate of the title compound, mp 204° C.

EXAMPLE 10

4-[1,2,5,6-Tetrahydro-1-(2-phenylethyl)-3-pyridinyl]-2-thiazolamine

By using (2-bromoethyl)benzene as the alkylating agent, and employing the methods of Examples 1 and 2, the title compound was obtained as its dihydrochloride monohydrate, mp 209°–211° C.

EXAMPLE 11

4-[1-(2-Ethoxyethyl)-1,2,5,6-tetrahydro-3-pyridinyl]-2-thiazolamine

The use of 2-bromoethyl ethyl ether, instead of 1-bromopropane, in the procedure described by Example 1 allowed the preparation of the title compound as an oil, which was converted into its dihydrochloride (mp 225°–230° C.) by the procedure described in Example 2.

EXAMPLE 12

N-[4-(1,2,5,6-Tetrahydro-1-pentyl-3-pyridinyl)-2-thiazolyl]acetamide

Seven grams of the 4-(1,2,5,6-tetrahydro-1-pentyl-3-pyridinyl)-2-thiazolamine obtained in Example 6 was dissolved in 100 ml of acetic anhydride with 10 g of anhydrous sodium acetate. The solution was heated at reflux under a nitrogen atmosphere for three hours. The solvent was removed on a rotary evaporator and the residue was partitioned between 150 ml dichloromethane and 150 ml 10% sodium bicarbonate solution. The organic layer was concentrated in vacuo and the residue was chromatographed on silica gel using 2% ammonium hydroxide in ethyl acetate as the eluent. The title compound was obtained as 4.10 g of a beige solid, mp 117°–120° C.

EXAMPLE 13

N-[4-(1,2,5,6-Tetrahydro-1-propyl-3-pyridinyl)-2-thiazolyl]-acetamide

Using the procedure described in Example 12 on the 4-(1,2,5,6-tetrahydro-1-propyl-3-pyridinyl)-2-thiazolamine prepared in Example 1, the title compound was obtained as a beige solid, mp 109°–112° C.

EXAMPLE 14

N-Methyl-4-(3-pyridinyl)-2-thiazolamine

3-Bromoacetylpyridine hydrobromide was prepared as described by A. Dornow, H. Machens, and K. Bruncken (*Chem. Ber.* 1951 (84), 147), from 3-acetylpyridine, and heated in water with 1.05 equivalents of N-methylthiourea for 30 minutes. After cooling, the solution was made basic by addition of ammonium hydroxide and N-methyl-4-(3-pyridinyl)-2-thiazolamine was obtained as an orange solid (mp 114°–116° C.) in 70% overall yield.

EXAMPLE 15

N-Methyl-4-(1,2,5,6-tetrahydro-1-propyl-3-pyridinyl)-2-thiazolamine

The procedure described in Example 1 was repeated, using the N-methyl-4-(3-pyridinyl)-2-thiazolamine prepared in Example 14 and an excess of 1-bromopropane as the reactants. The title compound was purified by column chromatography (65% yield) and converted to its HCl salt by the procedure of Example 2. The resulting salt (mp 138° C.) contained 1.25 molecules of HCl and one molecule of water.

EXAMPLE 16

N-methyl-4-(1,2,5,6-tetrahydro-1-pentyl-3-pyridinyl)-2-thiazolamine

The procedure of Example 1 was repeated, using the N-methyl-4-(3-pyridinyl)-2-thiazolamine prepared in Example 14 and an excess of 1-bromopentane as the reactants. The title compound was purified by column chromatography (53% yield) and converted to its HCl salt by the procedure of Example 2. The salt obtained (mp 168°–172° C.) contained 1.5 molecules of HCl and one molecule of water.

EXAMPLE 17

N-methyl-N-[4-(1,2,5,6-tetrahydro-1-pentyl-3-pyridinyl)-2-thiazolyl[-acetamide

By applying the method of Example 12 to the compound obtained in Example 16, the title compound was prepared as a tan solid, mp 78°–81° C.

EXAMPLE 18

4-(1-Propyl-3-piperidyl)-2-thiazolamine

Ethyl N-propylnipecotate (73.86 g) was dissolved in 500 ml ethanol, treated with lithium hydroxide monohydrate (15.57 g) at reflux for 24 hours. Upon evaporation and drying in vacuo (100° C., eight hours), lithium N-propylnipectotate was obtained (white powder; 60 g). A solution of 17.7 g of this salt in 200 ml THF was treated dropwise with one equivalent of methyl-lithium, at 0° C. After stirring at room temperature overnight, an aqueous work-up yielded 3-acetyl-N-propylpiperidine (mp of HCl salt 108°–111° C.). When 2.5 of this compound were intimately mixed with 2.28 g of thiourea and 3.81 g of iodine and heated on a steam bath for 24 hours, followed by a column chromatography (Silica; acetone) and salt formation by the procedure of Example 2, 1.75 g of 4-(1-propyl-3-piperidyl)-2-thiazolamine hydrochloride (mp 243°–248° C.) were obtained.

EXAMPLE 19

N-[4-(1-propyl-3-piperidyl)-2-thiazolyl]acetamide 4-(1-Propyl-3-piperidyl)-2-thiazolamine (1.8 g), prepared as described in Example 18, was refluxed in 8 ml acetic anhydride for two hours. An aqueous work-up was followed by a column chromatography (Silica; methanol) and salt formation by the procedure of Example 2. N-[4-(1-propyl-3-piperidyl)-2-thiazolyl]acetamide hydrochloride (1.3 g, mp 250°–5° C.) was obtained; this salt contained ¼ molecule of water.

We claim:

1. A compound having the structural formula

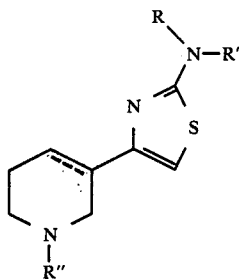

wherein ≡ signifies the presence of a single or double bond between two carbon atoms; R is H or a straight or branched alkyl of from one to four carbon atoms; R' is CO—R''' in which R''' is a straight or branched alkyl group of from one to four carbon atoms; R'' is a straight or branched alkyl group of from one to eight carbon atoms, a straight or branched alkenyl group of from two to eight carbon atoms, an aralkyl group wherein the aryl portion is phenyl or phenyl substituted by lower alkyl, lower alkoxy, lower thioalkoxy, halogen or trifluoromethyl and wherein the alkyl is straight or branched from one to four carbon atoms, or a group of the formula —$(CH_2)_n$—O—$(CH_2)_m$—$CH_3$ wherein n and m are independently zero to four; or the stereoisomers thereof when ≡ is a single bond, or a pharmaceutically acceptable acid addition salt thereof.

2. A compound according to claim 1 wherein R' is CO—R''' wherein R''' is a methyl group.

3. A compound according to claim 1 and being N-[4-(1,2,5,6-tetrahydro-1-pentyl-3-pyridinyl)-2-thiazolyl]-acetamide.

4. A compound according to claim 1 and being N-[4-(1,2,5,6-tetrahydro-1-propyl-3-pyridinyl)-2-thiazolyl]-acetamide.

* * * * *